US006410012B1

(12) United States Patent
Sizemore et al.

(10) Patent No.: US 6,410,012 B1
(45) Date of Patent: Jun. 25, 2002

(54) ANTIMICROBIAL MEDIATED BACTERIAL DNA DELIVERY

(75) Inventors: Donata R. Sizemore, Brentwood, MO (US); Jerald C. Sadoff, Washington, DC (US); Jason C. Grove, Ashton, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/049,566

(22) Filed: Mar. 27, 1998

Related U.S. Application Data

(60) Provisional application No. 60/042,090, filed on Mar. 28, 1997.

(51) Int. Cl.$^7$ .......................... A01N 63/00; A61K 48/00
(52) U.S. Cl. ................. 424/93.2; 424/93.4; 435/320.1; 435/245; 435/234
(58) Field of Search .......................... 514/44; 435/455, 435/320.1, 325, 69.1, 471, 234, 245; 424/93.2, 93.4

(56) References Cited

U.S. PATENT DOCUMENTS 5,824,538 A * 10/1998 Branstrom et al. ...... 435/252.1
5,877,159 A * 3/1999 Powell et al. .................. 514/44

OTHER PUBLICATIONS

Eck & Wilson, 'Gene–Based Therapy' in Goodman & Gilman's The Pharmacological Basis of Therapeutics, McGraw–Hill: New York, Ninth Edition, pp. 77–101.*

* cited by examiner

Primary Examiner—Dave T. Nguyen
Assistant Examiner—Brian Whiteman
(74) Attorney, Agent, or Firm—Elizabeth Arwine; Charles H. Harris

(57) ABSTRACT

This invention pertains in part to a method for delivering functional DNA or antigens. The desired DNA is introduced into attenuated bacteria able to enter cells. Once the bacteria is in the cell, antimicrobial agents are introduced such that they enter the mammalian cell and lyse the bacteria thereby allowing the delivery of carried functional DNA or antigens. The advantages of this method and its uses are described.

15 Claims, No Drawings

ANTIMICROBIAL MEDIATED BACTERIAL DNA DELIVERY

This application claims benefit to provisional No. 60/042,090 filed on Mar. 28, 1997.

INTRODUCTION

This invention relates to a method for introducing functional nucleic acids into cells using a bacterial delivery system. A bacterial vector capable of delivering functional nucleic acids to cells can be produced by introducing a bacterial plasmid containing promoters and other sequences containing instructions recognized by eukaryotic cells into bacteria capable of invading cells, being taken up by cells, or interacting with cells in such a way as to have the nucleic acids reach the eukaryotic cell cytoplasm. The nucleic acids delivered to the cell in this way can direct the eukaryotic cell to produce antigens or other functional molecules.

These unique bacterial delivery systems therefore can be used as vaccines to prevent or treat infectious diseases and cancer, down regulate the immune system in the case of tissue rejection in transplantation, prevent or treat autoimmune diseases and other diseases related to dysregulation of the immune system. In addition, the bacterial delivery systems can be used for gene therapy or gene replacement for treatment or amelioration of disease such as hereditary genetic diseases, cancers and virus infections.

Direct DNA-mediated immunization is another approach to the introduction of functional nucleic acids and vaccine development. Highly purified bacterial plasmid DNAs expressing desired proteins under the control of viral promoters have been injected primarily into muscle or skin by traditional needle and syringe or by other more exotic methods such as biolistic transfection with DNA-coated gold microparticles (for review see Donnelly, J. J. et al. *J. Immunol Methods* (1994) 176: 145) (All documents cited herein supra or infra are hereby incorporated by reference). Investigators using this technology have been able to elicit neutralizing antibodies, cytotoxic T lymphocytes and protection against challenge in several animal models of infection ranging from influenza to malaria. The use of bacteria as a delivery system as described in this invention is a unique method of delivering DNA to mammalian cells and has the potential to provide a simple, inexpensive way of extending DNA immunization to the local immune system and beyond through oral and other mucosal routes of immunization.

Previously, live bacteria have been utilized as vaccines in order to protect against subsequent infection. Attenuated or less virulent Shigella, Salmonella, Listeria, and other bacteria have been given orally to immunize against subsequent infection with more virulent forms of these bacteria. Likewise, attenuated bacterial and mycobacterial organisms such as Bacille Calmette-Guerin (BCG) have been administered parenterally to protect against related organisms such as *M. tuberculosis*. Genes from bacteria, viruses and parasites have been cloned into a variety of bacteria and mycobacteria for the purpose of directing the bacteria to express the foreign antigen or impart on the bacteria certain desired properties for use as a live vaccine. Examples include cloning the invasion genes of Shigella into the normally non-invasive *E. coli* rendering the *E. coli* invasive and therefore more suitable for use as a vaccine strain, or cloning of *P. falciparum* malaria genes into *Salmonella typhimurium* which subsequently express these malaria proteins and, following oral administration of the bacteria, induce specific cytotoxic T cell immunity and protection in mice against malaria challenge (Sadoff et al. *Science* (1988) 240 :336–338; Aggrawal et al. *J. Exp. Med.* (1990) 172:1083–1090). All of these bacterial delivery systems require the bacteria itself to produce the antigen or functional molecule and are dependent on a bacterium which is sufficiently attenuated to be safe for use in humans, but still able to induce a protective response. The bacterial delivery system of the present invention is designed to deliver functional nucleic acids which are then transcribed and translated as directed by the eukaryotic machinery to produce foreign antigens or functional molecules. In this case, antigen toxicity which is often seen when using live attenuated bacterial carriers expressing foreign proteins/peptides is eliminated because the expression occurs within the mammalian via its own machinery. This also will allow for any secondary modifications required of the protein; thus, permitting the protein to take a more charactistic/natural form for processing and presentation to the immune system or to direct a cellular function. In addition, if desired, it can be used to deliver prokaryotically produced antigens and functional molecules.

This invention can be applied to any desired bacteria. We chose Shigella as an example of a bacterial delivery system because of its ability to invade cells, escape from the endocytic vacuole, and enter into the cytoplasm of eukaryotic cells. These properties are not required of a bacteria chosen for application of the present invention, but simplified the experimental system. Shigellae are enteric pathogens that invade the human colonic epithelium and multiply intracellularly, causing bacillary dysentery. Bacillary dysentery is caused by all members of the genus Shigella (*S. boydii, S. dysenteriae, S. flexneri*, and *S. sonnei*). Shigellosis is prevalent in developing countries, but is also found in industrialized nations, especially in institutional settings. It has been estimated that Shigellosis is the cause of half a million deaths a year, mostly among children, making the development of a safe and effective Shigella vaccine important (Stole, B. J. et al. *J. Infect. Dis.* (1982) 146: 177). To cause dysentery, Shigella strains must be able to recognize, invade and multiply within epithelial cells of the colon (LaBrec, E. H. et al. *J. Bacteriol.* (1964) 88: 1503). Both the bacteria and host cell play a role in the invasive process wherein the host cell actively engulfs the bacteria which in turn escapes from the phagosome by a bacteria-mediated digestion of the phagosomal membrane (Sansonetti, P. J. et al. *Infect. Immun.* (1981) 34: 75). Once in the cell, bacterial multiplication occurs resulting in host cell necrosis.

SUMMARY

In this invention is described a method for delivering DNA to cells. The method of the present invention includes the introdution of the desired DNA into bacteria, allowing the bacteria to infect or enter cells, and then lysing the bacteria inside the cells such that the desired DNA is released. Even though a specific bacteria is described herein and is shown to deliver nucleic acids to eukaryotic cells, this invention is applicable to all bacteria and mycobacteria. Plasmids introduced into other cells such as plant cells may also render these cells capable of delivering nucleic acids.

Specifically, the method of the present invention uses an attenuated bacterial strain which is sufficiently attenuated to not cause disease, while still maintaining the ability to enter mammalian cells. The attenuated strain used in the method of the present invention does not carry genetic mutations specifically designed to lyse the carrier and mediate delivery of plasmid DNA. Since the bacterial strain is not engineered to lyse, delivery of the DNA in the cell is mediated by alternative methods, such as, for example, the use of antimicrobial agents. The *Shigella flexneri* strain used as a model in the present invention, SC602, carries mutations in the icsA gene required for intracellular spread and aerobactin (iuc:: iut) and was described in Barzu et al., *Infection and Immunity* 64: 1190–1194 (1996). Once the attenuated bacteria containing the DNA to be delivered is inside the cell, antimicrobials are introduced which eliminate the bacteria and allow the release of intact DNA into the cell.

The advantage of the method of the present invention is that any bacterial strain can be used; so long as the strain meets the following criteria: attenuated for use in humans or other animals, invasive, and exits or breaks down the endocytic or phagocytic vacuole in such a way as to allow the release of functional DNA. Therefore, one can take advantage of the higher level of invasiveness afforded other attenuated bacterial strains thereby increasing the number of mammalian cells infected, and thus the number of mammalian cells expressing the foreign protein or peptide once the bacteria is lysed inside the cell.

Therefore, it is one object of the invention to provide a delivery vehicle for the delivery of DNA to cells. The DNA encoding desired gene(s) or antigen(s) along with control sequences can be introduced into attenuated bacteria, and the recombinant attenuated strain allowed to enter mammalian cells afterwhich antimicrobials able to lyse the bacteria are introduced such that the bacteria is lysed and DNA delivery is mediated. Such a delivery vehicle could be used for oral and other mucosal immunization and gene therapy strategies.

It is another object of the present invention to provide a Shigella delivery vehicle for the delivery of DNA to mucosal surfaces. The DNA encoding desired gene(s) or antigen(s) can be introduced into attenuated Shigella, the recombinant attenuated Shigella strain allowed to enter mammalian cells, afterwhich, antimicrobials able to lyse the Shigella are introduced such that the Shigella is lysed and DNA delivery is mediated. Such a delivery vehicle could be used for oral and other mucosal immunization and gene therapy strategies.

It is still another object of the present invention to provide a method for the delivery of heterologous foreign antigens expressed by attenuated bacteria, more specifically Shigella, for the purpose of inducing in an individual an immune response against the foreign antigen or for treatment of a disease wherein said foreign antigen is missing or found in reduced amount.

It is further another object of the invention to provide a delivery vehicle for delivery of functional DNA and antigens to cells in vitro for use of those cells in, for example, transplantation and gene therapy. The DNA encoding desired gene(s) or antigen(s) can be introduced into attenuated bacteria, and the recombinant attenuated strain allowed to enter cells in vitro afterwhich, antimicrobials able to lyse the bacteria are introduced such that the bacteria is lysed and DNA delivery is mediated.

It is yet another object of the invention to provide a general method for introducing functional DNA into cells using bacterial delivery systems. The desired functional DNA is introduced into an attenuated bacteria able to enter or infect cells afterwhich, an antimicrobial is used to lyse the bacteria inside the cell such that the DNA is released in the cell. This method can be used for inducing protective immunity as a vaccine, for preventing and treating tumors, for the therapy and treatment of autoimmune disorders, for the treatment of conditions related to dysfunction of the immune system, for transplantation, for gene replacement, and gene therapy.

DETAILED DESCRIPTION

The present invention describes a method for delivery of DNA into cells. The method of the present invention comprises the steps of introducing the desired DNA along with control sequences into a bacteria able to enter cells, and then lysing the bacteria inside the cells such that the DNA is delivered and expressed by the cell. This process is generally applicable to all bacteria and mycobacteria.

By 'control sequences' is meant DNA sequences which are necessary to effect the expression of coding sequences to which they are operably linked. By 'operably linked' is meant a juxtaposition wherein the components are in a relationship permitting them to function in their intended manner. A control sequence 'operably linked' to a coding sequence is ligated in such a way that expression of the coding sequence is achieved under conditions compatible with the control sequences. Generally, such control sequences include promoter and ribosome binding site. Promoters can be specific for the cell type where the antigen is to be expressed. In addition, promoters can be constitutive, expressed continuously, or can be inducible such that the expression of the DNA or antigen can be regulated. The term 'control sequences' is intended to include, at a minimum, all components whose presence is necessary for expression, and may also include additional components whose presence is advantageous, for example, enhancers to increase expression of the antigen. Control sequences specific for different cell types and conditions are well known in the art. The combination of control sequences and desired DNA encoding the antigen of interest will be referred to hereafter as 'functional DNA'

Specifically, the present invention describes a method for delivery of functional DNA into cells, said method comprising introducing functional DNA into an attenuated Shigella strain, the Shigella allowed to invade and enter the eukaryotic cell, and then lysed inside the cell using antimicrobial agents capable of entering the cell and lysing the bacteria thereby releasing the desired functional DNA.

More specifically, the desired functional DNA encoding a desired antigen along with control sequences is introduced into SC602, an attenuated *Shigella flexneri*2a strain containing a deletion in the icsA gene required for intracellular spread and aerobactin (iuc::iut) [described in Barzu, et al., 1996, supra]. The recombinant SC602 is allowed to invade and enter the eukaryotic cells of the epithelial mucosa and antimicrobial agents are introduced which enter the infected eukaryotic cells and lyse the bacteria thereby releasing the functional DNA into the eukaryotic infected cells.

In accordance with the present invention, any attenuated bacterial strain can be used. The bacteria does not need to be virulent, but preferably should have the ability to enter or be taken up by the target cell and be attenuated to such an extent that clinical symptoms be acceptable. In addition, the bacteria must be sensitive to the antimicrobial to be used. Examples of such bacteria include Listeria, entreoinvasive *E. coli*, Ricketsia, or engineered *E. coli* spp., Salmonella spp., Vibrio spp., Klebsiella spp., Bordetella spp., Hemophilus spp., Brucella spp., Helicobacter spp., Bacillus spp., to name a few.

In accordance with the present invention, any gene or genes can be introduced into the bacterial chromosome or virulence plasmid by methods described above, or alternatively can be carried by the bacteria in a replicating or nonreplicating plasmid. The vectors of interest can be introduced via transformation, electroporation, transfection or conjugation. Genes for immunizations would include genes encoding foreign antigens from organisms causing, for example, diarrheal diseases such as rotavirus, sexually transmitted diseases such as human immunodeficiency virus, *Neisseria gonorrhoeae*, and human papilloma virus, and gastrointestinal diseases such as the ulcer causing *Helicobacter pyloni*. In the model of the present invention, the attenuated Shigella was shown to deliver functional DNA and antigens to cells.

Specifically, the use of Shigella, as a bacterial delivery may permit mucosal immunization simultaneously with multiple antigens that can be directed for class I and/or class II presentation, stimulation of Th1 or Th2 help, or secreted while maintaining the proper folding and conformational epitopes for IgA and IgG antibody production.

Similar methods can be used for the delivery of functional DNA for gene therapy and correction of inborn errors of metabolisms. Such genes would include, for example, replacement of defective genes such as the CFTR gene for cystic fibrosis or introduction of new genes such as reverse transcriptase or protease antisense genes for the treatment of HIV or genes to upregulate Th1 immune responses such as interleukin-12 (IL-12) or genes to up- or down-regulate certain receptors, metabolites or hormones such as cholesterol and cholesterol receptors, insulin and insulin receptors, or genes encoding products that can kill cancer cells such as Tumor Necrosis Factor (TNF), or genes to upregulate systems that have decreased for a variety of reasons including aging such as secretion of growth hormone, stimulation of osteocytes to promote bone growth, and down regulation of osteoclasts to decrease bone desorption.

Delivery of functional DNA can also be used to downregulate the immune system in an antigen specific manner or general manner in order to prevent or control autoimmune diseases or other diseases involved in dysregulation of the immune system or for prevention or treatment of specific diseases or conditions including transplantation. Examples include the prevention or treatment of autoimmune encephalitis, multiple sclerosis, lupus erythematosis, diabetes melitus, Crohn's disease and other inflammatory bowel diseases, and rheumatoid arthritis and other inflammatory joint and skin diseases. Other examples include down regulation of immune responses that inhibit appropriate protective or curative immune responses such as down regulation of immune responses that distract from protective and curative immune responses to cancer and other diseases. For example, down regulation of Th2 responses when Th1 responses are appropriate for prevention and treatment of cancer, Leishmania, *Mycobacterium tuberculosis*, and HIV. This can be accomplished using this methodology through manipulation of the unique immunosuppressive properties of the gut and other local immune systems in combination with the ability to code for production of the appropriate cytokine milieu for induction of the appropriate immune response and suppression of inappropriate responses.

In accordance with the present invention, the bacteria is lysed inside the cell to release and deliver the desired functional DNA. Methods for lysing bacteria inside cells include the use of a drug or antimicrobial agent capable of entering the cells to a sufficient level, and has the properties of affecting the synthesis of the bacterial cell wall or other bacterial cell membrane component, or able to form holes/pores in the bacterial cell wall or membrane. Antimicrobial agents include any agent which inhibits the growth of or kills the bacteria. The agent can be manmade or produced or derived from a living organism such as an antibiotic. For a list of bacteria and the antibiotics given as treatment, please see G. L. Mandell, R. G. Douglas Jr, J. E. Bennett. *Principles and Practices of Infectious Diseases*. 3rd ed. New York: Churchill Livingstone, 1990. Early antimicrobial research yielded a very effective drug for treating Shigella and other intracellular bacteria, azithromycin [Kitzis et al. (1990) *J. Antimicrob. Chemother*. 25: Suppl.A. 15–18; Gordillo et al. (1993) *Antimicrobial Agents and Chemotherapy* 37:1203–1205]. Azithromycin is biochemically similar to erythromycin; it prevents the ribosome from ejecting the P-site tRNA and moving on to replace it with the A-site tRNA during transcription, thus inhibiting protein synthesis (Retsema, 1987). Its advantage over erythromycin is that it enters the mammalian cell at a higher concentration; therefore intracellular bacteria are killed more efficiently [Gladue et al. (1989) *Antimicrobial Agents and Chemotherapy* 33: 277–282; Gladue and Snider (1990) *Antimicrobial Agents and Chemotherapy* 34: 1056–1060; McDonald and Prull (1991) *Eur. J. Microbiol. Infect. Dis*. October 1991: 828–833].

The concentration and time of addition of the antimicrobial can be determined empirically for each bacterium. The time of addition of an antimicrobial agent is based upon the time when the bacteria leaves the endocytic vacuole (preferably after the bacteria have exited the endocytic vacuole, and prior to the destruction of the cultured cell). The concentration to be added should be an amount able to enter cells and act on the bacterium.

In another embodiment, the present invention relates to a method for the introduction of antigens of interest into cells. Such a method would comprise introduction of the desired functional DNA or antigen into attenuated bacteria, for example Shigella, such that the desired antigens are produced, administering said bacteria to an individual, and administering a bacterial lysing agent or antimicrobial such that the bacteria is lysed in the cell and antigens are introduced into the cell. Said antigens can be produced during the life cycle of the bacteria prior to entering said cells. These antigens can be expressed from a prokaryotic promoter, and can either be constitutively expressed or induced. Such genes include those from parasitic organisms for which an immune response is desired.

In another embodiment, the present invention relates to a method for the introduction of DNA or antigens of interest into cells in vitro. Such a method would comprise introduction of the desired functional DNA or antigen into attenuated bacteria such that the desired antigens are produced, administering said bacteria to cells, and lysing said bacteria in cells thereby mediating delivery of DNA or antigens of interest into cells. The bacteria chosen as a delivery vehicle would depend on the cell type into which the functional DNA is to be introduced. Shigella, for example infects several different cells types, such as BHK (baby hamster kidney cells), HeLa (Human cervical epitheloid carcinoma), and CaCo-2 (human colonic adenocarcinoma) and is therefore capable of delivering desired DNA or antigens into these cells wherein said DNA can be expressed. Cells into which functional DNA has been delivered can be transplanted for therapeutic purposes, used for gene therapy or used as reagents in diagnostic assays.

Current methods for introducing functional DNA or antigens into cells in vitro require purified DNA in ug amounts. The functional DNA is then added to their liposomes or other matrix, allowed to mix, then added onto the cells. The mixture is usually toxic to cells and may require several attempts to adjust the amount or ratio of functional DNA and matrix such that the DNA-matrix mixture is taken up by the cells. The method of the present invention presents advantages in that a bacterial strain or strains can be designed in which the investigator can do their desired cloning and selection. This strain would then act as a delivery vehicle to carry their cloned product to cultured mammalian cells with no need to purify the DNA and the clone containing the desired functional DNA selected in a short period of time.

Another embodiment of the present invention is the use of the method as a vaccine delivery system. The attenuated bacterial strain containing the functional DNA of interest can be used as an immunizing agent against infection. The attenuated bacterial vaccine of the present invention can be prepared in the form of a mixed vaccine which contains one strain or several different strains of attenuated bacteria with the same or a different DNA for each to deliver to the same cell or a different cell by selecting bacteria which are capable of infecting the target cell. Further, the vaccine can include at least one other antigen as long as the added antigen does not interfere with the effectiveness of the attenuated bacterial vaccine and the side effects and adverse reactions, if any, are not increased additively or synergistically. Once the functional DNA encoded immunogen is released in the cells as a result of lysing the bacteria, the cell is capable of producing the antigen, presenting it to the immune system for production of protective antibodies and/or cellular mediated immunity.

Vaccines are prepared for oral administration, either as liquid solutions or suspensions; solid form suitable for solution in, or suspension in, liquid prior to administration. The preparation may also be emulsified, or the ingredients are often mixed with excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations, nose drops or powders and contain about $10-10^{12}$ attenuated bacteria.

Vaccines can also be in the form of injectables. Suitable excipients would include, for example, saline or buffered saline (pH about 7 to about 8), or other physiologic, isotonic solutions which may also contain dextrose, glycerol or the like and combinations thereof. However, agents which disrupt or dissolve lipid membranes such as strong detergents, alcohols, and other organic solvents should be avoided. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine(thr-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and TIBI, which contains three components extracted from bacteria, monophosphoryl lipid A, trehalose dimycolate and cell wall skeleton (MPL+TDM+CWS) in a 2% sqalene/Tween 80 emulsion. The effectiveness of an adjuvant may be determined by measuring the level of desired immune response directed against the bacteria, carried antigen, or DNA encoded antigen resulting from administration of the attenuated bacteria, in vaccines which are also comprised of the various adjuvants.

The vaccine can be administered in the form of a liquid or suspension prepared as discussed above. Additional formulations which are suitable for other modes of administration include suppositories. Additionally, the vaccine can be lyophilized. For suppositories, traditional binders and carriers may include, for example, polyalkylene glycols or triglycerides; such suppositories may be formed from mixtures containing the attenuated bacteria enough to generate the desired immune response, i.e., protection or reduction of disease incidence or severity without causing undesirable, adverse side affects, generally in a range of $10-10^{12}$ colony forming units of attenuated bacteria per dose.

Generally, the vaccine may be administered orally, subcutaneously, intradermally, or intramuscularly in a dose effective for the production of the desired immune response. The vaccines are administered in a manner compatible with the dosage formulation, and in such amount as will be prophylactically and/or therapeutically effective. The quantity to be administered, which is generally in the range of or to $10-10^{12}$ colony forming units of attenuated and/or attenuated/inactivated bacteria per dose, depends on whether it is acting as a vaccine to bacteria or a carrier of heterologous antigens or DNA, on the subject to be treated, capacity of the subject's immune system to develop the desired immune response, and the degree of protection desired. Precise amounts of the vaccine to be administered may depend on the judgement of the practitioner and may be peculiar to each subject, antigen, or use of the bacteria as a vaccine or carrier.

The vaccine may be given in a single dose schedule, or preferably a multiple dose schedule in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. The dosage regimen will also, at least in part, be determined by the need of the individual and be dependent upon the judgment of the practitioner. Examples of suitable immunization schedules include: (i) 0, 1 month and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms or reduce severity of disease.

Described below are examples of the present invention which are provided only for illustrative purposes, and not to limit the scope of the present invention. In light of the present disclosure, numerous embodiments within the scope of the claims will be apparent to those of ordinary skill in the art.

The following MATERIALS AND METHODS were used in the examples that follow.

Bacteria: The attenuated vaccine strain of *Shigella flexneri*2a strain 2457T, 15D and 15D(pCMVβ) has been described elsewhere (Sizemore et al. (1995) *Science*270:299–302). Briefly, 15D carries a mutation in the asd gene and is therefore genetically programmed to die when it tries to divide. The Shigella strain SC602 was obtained from P. Sansonetti. pCMBβ expresses *E. coli* β-galactosidase under the control of the immediate early promoter and enhancer from the human cytomegalovirus (CMV) in mammalian cells, which permitted us to easily analyze mammalian-mediated gene expression after delivery [MacGregor and Caskey (1989) *Nucl. Acids Res.* 17:2365].

Mammalian Cells: The cell line used throughout these experiments was that of the baby hamster kidney (BHK) obtained from ATCC. BHK cells were grown in complete Dulbecco's Modified Eagle's Medium, DMEM (Biowhittaker), containing 10% newborn calf serum and 1% L-glutamine. These adherent cells were grown on polystyrene tissue culture ware at 37° C. and 5% $CO_2$. Cells are routinely used at a time when semi-confluence is reached.

Antibiotics: Powdered purified azithromycin was obtained from Maj. Kyle. Oral formulation of ciprofloxacin was obtained from Maj. Fleckenstein.

Reagents to measure β-galactosidase activity:

Phosphate buffered saline: 8.5 g/L NaCl, 5.75 g/L $Na_2HPO_4$, 1.0 g/L $KH_2PO_4$, sterile filtered.

PM-2 buffer: 20 mM $NaH_2PO_4$, 80 mM $NaHPO_4$, 0.1 mM $MnCl_2$, 2 mM $MgSO_4$, 40 mM β-mercaptoethanol, pH 7.3, sterile filtered.

ONPG reagent: 4 mg/ml o-Nitrophenyl-β-D-Galactopyranoside in PM-2 buffer.

Dissociation buffer: 8 M urea, 100 mM Tris, 5% SDS

Edda Twiddy's EDTA: 0.5 g EDTA, 0.4 g NaCl, 0.4 g KCl, 0.05 g $NaH_2PO_4$, 0.06 g $KH_2PO_4$ in 1 liter water, pH 7.6, sterile filtered The protocol used for these experiments consisted of diluting an overnight culture of the bacteria 1 in 50 and allowing it to grow to midlog phase, approximately 2.5 hours. The midlog cultures were then concentrated in Hank's Balanced Salts by centrifugation to approximately $10^9$ bacteria per milliliter and a small aliquot was taken to determine the midlog bacterial count. Two milliliters of bacteria were added to the appropriate semi-confluent flask of BHK cells and allowed to incubate for ninety minutes at 37° C. and 5% $CO_2$. After the incubation, the cells were rinsed with Hank's Balanced Salts (Sigma). In most cases the flasks were treated with complete DMEM containing 20 mg/ml gentamicin to kill all extracellular bacteria. Either antibiotic was then added at the designated time.

Demonstration of DNA Delivery

Harvesting of cells was carried out as follows. At the appropriate time point media was removed from the flasks and the flasks were rinsed thoroughly with Hank's Balanced Salts followed by Edda Twiddy's EDTA. Flasks were then treated with 5 milliliters of Trypsin-EDTA for 5 minutes at 37° C. and 5% $CO_2$ to lift the adherent mammalian cells from the flask. Ten milliliters of room temperature DMEM with serum was added to inactivate the Trypsin-EDTA. The cells were pelleted at 2000 rpm for 12 minutes at room temperature and resuspended in 10 milliliters of phosphate buffered saline (PBS).

A 100 μl aliquot was taken and diluted in 0.1% Triton X-100 and plated on diaminopimelic acid (DAP) supplemented congo red (Sigma) tryptic soy agar for 15D or TSA without DAP for SC602. The remainder was again pelleted and resuspended in 1.3 ml PM-2 buffer. 30 μl of 10% Triton X-100 was added and the sample was incubated at room temperature and vortexed frequently for ten minutes to lyse the BHK cells. The cellular debris was pelleted for minutes at 13500×g and 4° C.

Four hundred microliters of the supernatant was combined with 400 μl of PM-2 buffer in a spectrophotometric cuvette and allowed to equilibrate to 37° C. 200 μl of ONPG reagent is then added to each sample and any applicable standards. The samples were incubated at 37° C. and timed until a vibrant yellow color appeared, at which point the reaction was complete. The absorbance of each sample was measured at 420 nm and recorded. β-galactosidase activity was calculated as Ab420×380/Time (minutes). To determine the total amount of protein present in each assayed sample 200 μl of cold (−20° C.) acetone was added to 50 μl of the above supernatants, vortexed thoroughly and stored at −20° C. for 30 minutes. The samples were then pelleted for 10 minutes at 14000 rpm and the supernatant was discarded. Samples were allowed to dry in a heated evacuating centrifuge and then resuspended in 50 μl dissociation buffer. The protein concentration was then determined using a standard BCA (Pierce) protein determination protocol. Results are reported as β-galactosidase activity per mg of protein.

EXAMPLE 1

Use of Azithromycin to Mediate DNA Delivery

Early antibiotic research yielded a very effective drug for treating Shigella and other intracellular bacteria, azithromycin (Kitzis, 1990, supra; Gordillo, 1993, supra). Azithromycin is biochemically similar to erythromycin; it prevents the ribosome from ejecting the P-site tRNA and moving on to replace it with the A-site tRNA during transcription, thus inhibiting protein synthesis [Retsema et al. (1987) *Antimicrob. Agents Chemother.* 31: 1939–1947]. Its advantage over erythromycin is that it enters the mammalian cell at a higher concentration; therefore intracellular bacteria are killed more efficiently (Gladue, 1989, 1990, supra; McDonald and Prull, 1991, supra). For these experiments, complete DMEM containing the designated concentrations of the azithromycin were added to flasks of infected BHK cells at various times to determine an effective inhibitory concentration and the appropriate time for addition of the antibiotic to mediate DNA delivery (Table 1A). Treated cells were harvested within 24 hours of introducing the azithromycin. Results of β-galactosidase assays performed on cell lysates of BHK cells infected with either SC602 or SC602 (pCMVβ) treated with azithromycin revealed an observable amount of activity only from those cells that had been infected with SC602(pCMVβ) and treated with azithromycin. The results also indicated that addition of the azithromycin 1 to 2 hours after the adherence and invasion step greatly increased the amount of β-galactosidase activity detected as compared to those monolayers treated just after the adherence/invasion step. At this time the bacteria have had the greatest chance to leave the endocytic vacuole and most likely inhabit the cytoplasm at the time the antibiotic begins to act; thus the plasmid DNA is in the appropriate cellular compartment to make its way to the nucleus.

TABLE 1A

Azithromycin-mediated bacterial plasmid DNA delivery.

| Experiment | Strain | β-galactosidase activity/mg U/mg | Bacterial Counts Bact./Flask |
|---|---|---|---|
| Midlog | SC602 | | $1.7(10^9)$ |
| Midlog | SC602 pCMVβ | | $1.4(10^9)$ |
| 24 hr gentamicin, no azith. | SC602 | 0 | $6.4(10^4)$ |
| 24 hr gentamicin, no azith | SC602 pCMVβ | 0 | $3.5(10^4)$ |
| azith 30 μg/ml at time 0 | SC602 | 0 | $2.7(10^4)$ |

TABLE 1A-continued

Azithromycin-mediated bacterial plasmid DNA delivery.

| Experiment | Strain | β-galactosidase activity/mg U/mg | Bacterial Counts Bact./Flask |
|---|---|---|---|
| azith 30 μg/ml at time 0 | SC602 pCMVβ | 6.2 | 5.4(10⁴) |
| azith 60 μg/ml at time 0 | SC602 | 0 | 8.0(10⁴) |
| azith 60 μg/ml at time 0 | SC602 pCMVβ | 7.7 | 10.1(10⁴) |
| azith 120 μg/ml at time 0 | SC602 | 0 | 2.3(10⁴) |
| azith 120 μg/ml at time 0 | SC602 pCMVβ | 8.5 | 5.4(10⁴) |
| azith 30 μg/ml at time 1 hour | SC602 | 0 | 1.5(10⁴) |
| azith 30 μg/ml at time 1 hour | SC602 pCMVβ | 26.0 | 1.8(10⁴) |
| azith 60 μg/ml at time 1 hour | SC602 | 0 | 9.2(10³) |
| azith 60 μg/ml at time 1 hour | SC602 pCMVβ | 25.6 | 4.0(10²) |
| azith 30 μg/ml at time 2 hours | SC602 | 0 | 1.3(10⁴) |
| azith 30 μg/ml at time 2 hours | SC602 pCMVβ | 18.6 | 5.7(10⁴) |
| azith 60 μg/ml at time 2 hours | SC602 | 0 | 5.8(10³) |
| azith 60 μg/ml at time 2 hours | SC602 pCMVβ | 27.0 | 4.9(10³) |

Mid log counts indicate the number of bacteria added to the flask. Bacteria were allowed to interact with the monolayer for 90 minutes prior to extensive washing, and addition of gentamicin. Azithromycin was added at the indicated concentration and time after the adherence/invasion step. β-galactosidase assay was performed the following day.

EXAMPLE 2

For this experiment, BHK cells were infected with either 15D, 15D(pCMVb), SC602 or SC602(pCMVb). Initially, the number of viable bacteria and b-galactosidase activity were determined directly after the adherence and invasion step or 24 hours later in the presence of gentamicin. These results indicate: 1) strain SC602 can adhere and invade as well as strain 15D, which requires the presence of DAP in the inoculum to obtain this level of adherence and invasion and 2) only strain 15D(pCMVb) can deliver DNA in the absence of antibiotics. With the addition of 30 ug/ml azithromycin, SC602(pCMVb) can now deliver DNA with resulting b-galactosidase activity detected at a similar level to strain 15D(pCMVb) (i.e. 17.4 and 34 units versus 13.23 and 61.64 units). Addition of azithromycin immediately after the adherence and invasion step seemed to reduce the level of delivered DNA as indicated by the lower b-galactosidase units for both 15D(pCMVb) and SC602 (pCMVb). This reduction in b-galactosidase activity when azithromycin is added immediately after the adherence and invasion step can also be seen in Table 1 A. These results likely indicate that the bacteria are not within the cytoplasm at the time azithromycin begins to act; therefore, the plasmid DNA is released into the vacuole.

TABLE 1B

Azithromycin-mediated bacterial plasmid DNA delivery.

| Experiment | Strain | β-galactosidase activity/mg protein U/mg | Bacterial counts Bact./Flask |
|---|---|---|---|
| Adherence/invasion (90 min) | SC602 | 1.28 | 2.68(10⁶) |
| Adherence/invasion (90 min) | SC602(pCMVβ) | 0.69 | 4.88(10⁶) |
| Adherence/invasion (90 min) | 15D | 0.62 | 3.65(10⁶) |
| Adherence/invasion (90 min) | 15D(pCMVβ) | 1.30 | 0.97(10⁶) |
| 24 hours | SC602 | 1.17 | 0.13(10⁶) |
| 24 hours | SC602(pCMVβ) | 1.59 | 0.20(10⁶) |
| 24 hours | 15D | 0.74 | 0.18(10⁶) |
| 24 hours | 15D(pCMVβ) | 78.96 | 0.14(10⁶) |
| 30 μg/ml azithromycin added at indicated time after adherence/invasion: | | | |
| Immediately | SC602 | 0.79 | 0.19(10⁶) |
| Immediately | SC602(pCMVβ) | 17.40 | 0.23(10⁶) |
| Immediately | 15D | 0.74 | 0.11(10⁶) |
| Immediately | 15D(pCMVβ) | 13.23 | 0.03(10⁶) |
| 2 hours | SC602 | 0.83 | 0.09(10⁶) |
| 2 hours | SC602(pCMVβ) | 34.27 | 0.41(10⁶) |
| 2 hours | 15D | 1.03 | 0.02(10⁶) |
| 2 hours | 15D(pCMVβ) | 61.64 | 0.08(10⁶) |

Bacteria were allowed to interact with the monolayer for 90 min prior to extensive washing, and addition of gentamicin. After the adherence/invasion step, 30 μg/ml of azithromycin was added immediately or 2 hours after the adherence/invasion step. β-galactosidase activity was measured the following day.

Results from Tables 1 A and B indicate cultured cells that have been infected with an attenuated strain of bacteria not designed to lyse on its own can be made to do so by the addition of exogenous azithromycin. Addition should be timed to allow maximum DNA delivery (i.e. approximately 2 hours post adherence and invasion). It should be noted that no dramatic decrease in the number of viable bacteria was detected after the addition of azithromycin indicating: 1) a longer exposure time to the antibiotic might be necessary to lyse all of the bacteria, 2) other conditions may need to be in place to mimic true physiological conditions, or more likely 3) the level of replication in the absence of antibiotics (i.e. the 24 hour data) may not be a true reflection of the viable bacteria if this strain is destroying the cultured cells, an observation that need to be clarified.

EXAMPLE 3

Ciprofloxacin Treatment to Mediate DNA Delivery

In these studies, strains 15D, 15D (pCMVβ), SC602, and SC602 (pCMVβ) were allowed to invade BHK cells cultured to semi-confluence. They were uniformly treated with gentamicin, an antibiotic that readily kills any remaining extracellular bacteria, then treated at various times with ciprofloxacin [Fass, R. (1983) *Antimicrobial Agents and Chemotherapy* 24: 568–574], a quinolone capable of inhibiting the activity of DNA gyrases which are required to supercoil bacterial DNA [Gellert et al. (1976) *Proc. Natl. Acad. Sci.* 73(11): 3872–3876]. The supercoiled structure of DNA is responsible for the protection and proper functioning of the DNA. Unless supercoiled, DNA cannot transcribe properly and is also exposed to destructive nucleases and other damaging agents found within the bacterial cell. Unlike the results described above, ciprofloxacin was unable to mediate DNA delivery (Table 2). The best explanation for these results is that ciprofloxacin inhibits the ability of DNA gyrases to supercoil the plasmid DNA; thus the plasmid DNA is not protected from nucleases during the period in which the bacterium is dying. In fact, treatment of 15D (pCMVβ) infected monolayers with ciprofloxacin just after the adherence/invasion step inhibited delivery of the plasmid DNA by this strain. This could be the result of either the bacteria not being out of the endocytic vacuole at the time of their death or as suggested above- ciprofloxacin's action on DNA gyrases affects the supercoiling of the plasmid DNA making it more susceptible to nuclease activity. If the latter is true, the results would also suggest strain 15D has lysed and delivered the plasmid DNA by two hours after the adherence and invasion step.

TABLE 2

Ciprofloxacin treatment.

| Experiment | Strain | β-galactosidase activity/mg of protein U/mg | Bacterial Counts Bact./Flask |
|---|---|---|---|
| Midlog | 15D | | 1.6(10⁹) |
| Midlog | 15D pCMVβ | | 1.7(10⁹) |
| Midlog | SC602 pCMVβ | | 2.2(10⁹) |
| Midlog | SC602 pCMVβ | | 1.3(10⁹) |
| 90 min. adherence/invasion | 15D | 1.01 | 6.6(10⁵) |
| 90 min. adherence/invasion | 15D pCMVβ | 1.64 | 6.8(10⁶) |

TABLE 2-continued

Ciprofloxacin treatment.

| Experiment | Strain | β-galactosidase activity/mg of protein U/mg | Bacterial Counts Bact./Flask |
|---|---|---|---|
| 90 min. adherence/invasion | SC602 | 0.15 | 2.8(10⁶) |
| 90 min. adherence/invasion | SC602 pCMVβ | 1.02 | 7.2(10⁶) |
| 24 hr gentamincin, no cipro. | 15D pCMVβ | 188.24 | 1.56(10⁴) |
| 24 hr gentamincin, no cipro. | SC602 pCMVβ | 1.40 | 6.02(10⁴) |
| cipro, added at time 0 24 hr gentamicin | 15D pCMVβ | 7.56 | 0 |
| cipro, added at time 0 24 hr gentamicin | SC602 pCMVβ | 1.67 | 1(10³) |
| cipro, added at time 2 hours 24 hr gentamicin | 15D pCMVβ | 131.48 | 0 |
| cipro, added at time 2 hours 24 hr gentamicin | SC602 pCMVβ | 2.34 | 2(10²) |
| cipro, added at time 4 hours 24 hr gentamicin | 15D pCMVβ | 228.20 | 1.2(10³) |
| cipro, added at time 4 hours 24 hr gentamicin | SC602 pCMVβ | 1.48 | 0 |

Midlog counts indicate the number of bacteria added to each flask. Bacteria in each expeiment were allowed to interact with the monolayer for 90 minutes prior to extensive washing, followed by the addition of gentamicin (50 µg/ml) or ciprofloxacin (50 µg/ml) containing medium at the indicated time.

EXAMPLE 4

Cyclohexamide Treatment Confirms Production of the Plasmid-encoded Foreign Product is Dependent upon the Eukarvotic Cell In these experiments, BHK cells were infected with 15D(pCMVβ) for 90 minutes then treated with gentamicin followed by cyclohexamide, a peptidyl transferase blocker that inhibits protein synthesis in eukaryotic cells but not in bacteria. These experiments were done to confirm translation of the plasmid-encoded β-galactosidase was dependent upon the eukaryotic cell machinery, (i.e., protein synthesis was not taking place in the bacterial cell). As illustrated in Table 3, treatment of 15D(pCMVβ) infected BHK cells with cyclohexamide at various times after the adherence/invasion step resulted in the inhibition of β-galactosidase activity, yet had little (i.e, a loss of 1 log viable bacteria when treatment occurred right after to two hours after the adherence/invasion step) to no effect on the number of viable bacteria recovered from treated wells. This may be due to an active process that the bacteria requires from the cultured cell which is inhibited by the addition of cyclohexamide allowing fewer bacteria to enter.

TABLE 3

Effect of cyclohexamide on bacterial-mediated plasmid DNA delivery.

| Experiment | Strain | β-galactosidase activity/mg U/mg | Bacterial Counts Bact./Flask |
|---|---|---|---|
| Midlog | 15D | | 9.4(10⁸) |
| Midlog | 15D p pCMVβ | | 1.8(10⁹) |
| 24 hrs gent | 15D | 1.31 | 1.1(10⁴) |

TABLE 3-continued

Effect of cyclohexamide on bacterial-mediated plasmid DNA delivery.

| Experiment | Strain | β-galactosidase activity/mg U/mg | Bacterial Counts Bact./Flask |
|---|---|---|---|
| 24 hrs gent | 15D pCMVβ | 302.5 | $4.2(10^4)$ |
| cyclohexamide at time 0 | 15D pCMVβ | 7.56 | $3.8(10^3)$ |
| cyclohexamide at time 2 hours | 15D pCMVβ | 5.82 | $4.0(10^3)$ |
| cyclohexamide at time 4 hours | 15D pCMVβ | 4.96 | $4.5(10^4)$ |

Mid-log indicates the number of bacteria added per flask. Bacteria are allowed to interact with the monolayer for 90 minutes followed by washing and addition of gentamincin. Cyclohexamide is added at the indicated time after the adherence/invasion step. The β-galactosidase assay was performed the following day.

DISCUSSION

Azithromycin is capable of mediating bacterial-based plasmid DNA delivery by an attenuated strain of *Shigella flexneri* not programmed to lysis after entry and endocytic vacuole escape of a mammalian cell. We hypothesize azithromycin action on protein synthesis inhibits the bacterium from synthesizing many of the components required to build its cell wall during division—much like the mutation of the asd gene within strain 15D, which removes an enzyme required to complete the process of cell wall synthesis. Thus, the plasmid DNA leaks out of the dying bacterium into the mammalian cell cytoplasm. We hypothesize that ciprofloxacin's inability to mediate delivery is based on the drug's action on DNA gyrase. If the plasmid DNA is no longer protected from the action of bacterial nucleases, then it will be degraded before the bacterium lyses.

What is claimed is:

1. A method of delivering a functional DNA into a cell in vitro, said method comprising (i) introducing a functional DNA into attenuated bacteria able to enter cells;

(ii) allowing said attenuated bacteria to enter said cell; and (iii) administering an antimicrobial to the cell of step (ii), wherein said antimicrobial enters said cell resulting in lysis of said bacteria inside said cell such that said functional DNA is released into said cell.

2. The method for the delivery of a functional DNA according to claim 1, wherein said bacteria is Shigella.

3. The method for the delivery of a functional DNA according to claim 2 wherein said Shigella is SC602.

4. The method for the delivery of a functional DNA according to claim 1, wherein said antimicrobial is an antibiotic.

5. The method for the delivery of a functional DNA according to claim 4, wherein said antibiotic is azithromycin.

6. The method for the delivery of a functional DNA according to claim 1 wherein said cell is a mucosal epithelium cell.

7. The method for the delivery of a functional DNA according to claim 6, wherein said cell is an intestinal mucosal epithelium cell.

8. A DNA delivery kit for the delivery of a functional DNA into cells, said kit comprising attenuated Shigella containing functional exogenous DNA, and an antimicrobial that functions to enter said cells and lyse said attenuated Shigella.

9. A method of delivering a functional DNA into a mucosal cell, said method comprising (i) introducing a functional DNA into attenuated bacteria able to enter cells;

(ii) administering the attenuated bacteria of step (i) to a mucosal cell, thereby allowing the attenuated bacteria to enter said cell; and (iii) administering an antimicrobial to the cell of step (ii), wherein said antimicrobial enters said cell, thereby resulting in lysis of said bacteria inside said cell such that said functional DNA is released into said cell.

10. The method for the delivery of a functional DNA according to claim 9, wherein said bacteria is Shigella.

11. The method for the delivery of a functional DNA according to claim 10 wherein said Shigella is SC602.

12. The method for the delivery of a functional DNA according to claim 9, wherein said antimicrobial is an antibiotic.

13. The method for the delivery of a functional DNA according to claim 12, wherein said antibiotic is azithromycin.

14. The method for the delivery of a functional DNA according to claim 9 wherein said cell is a mucosal epithelium cell.

15. The method for the delivery of a functional DNA according to claim 14, wherein said cell is an intestinal mucosal epithelium cell.

* * * * *